United States Patent [19]
Fischer et al.

[11] Patent Number: 5,683,711
[45] Date of Patent: Nov. 4, 1997

[54] ACTIVE INGREDIENT PATCH

[75] Inventors: Wilfried Fischer; Karin Klokkers, both of Holzkirchen, Germany

[73] Assignee: Hexal Pharma GmbH, Holzkirchen, Germany

[21] Appl. No.: 535,038

[22] PCT Filed: Apr. 20, 1994

[86] PCT No.: PCT/EP94/01231

§ 371 Date: Dec. 15, 1995

§ 102(e) Date: Dec. 15, 1995

[87] PCT Pub. No.: WO94/23707

PCT Pub. Date: Oct. 27, 1994

[30] Foreign Application Priority Data

Apr. 20, 1993 [DE] Germany ............... 43 12 818.1
Nov. 18, 1993 [DE] Germany ............... 43 39 400.0

[51] Int. Cl.⁶ ............... A61F 13/00; A61K 9/70; A61K 9/14

[52] U.S. Cl. ............... 424/449; 424/487

[58] Field of Search ............... 424/449, 487

[56] References Cited

U.S. PATENT DOCUMENTS

| | | | |
|---|---|---|---|
| 4,913,905 | 4/1990 | Fankhauser et al. | 424/449 |
| 5,128,124 | 7/1992 | Fankhauser et al. | 424/449 |
| 5,204,119 | 4/1993 | Shiobara et al. | 424/489 |
| 5,300,291 | 4/1994 | Sablotsky et al. | 424/78.18 |
| 5,352,457 | 10/1994 | Jenkins | 424/448 |

*Primary Examiner*—Thurman K. Page
*Assistant Examiner*—Kathryne E. Shelborne
*Attorney, Agent, or Firm*—Burgess, Ryan & Wayne

[57] ABSTRACT

The invention relates to an active ingredient patch in the form of a laminate, the patch comprising a carrier and a matrix of a single polymer and if appropriate another polymer and vitamin E.

10 Claims, 11 Drawing Sheets

IN VITRO RELEASE OF OESTRADIOL / NETA TTS

| TIME (h) | TIME 0.5 | RELEASE | | | | RATE (mg/hour) | | | RATE (mg/hour 0.5) | | | |
|---|---|---|---|---|---|---|---|---|---|---|---|---|
| | | ENA 007 OESTRA-DIOL | ENA 700 NETA | ENA 007 OESTRA-DIOL | ENA 700 NETA | ENA 007 OESTRA-DIOL | % DIFF-ERENCE OESTRA-DIOL | ENA 700 NETA | % DIFF-ERENCE NETA |
| 0 | 0 | 0.00 | 0.00 | 0.00 | 0.00 | 0.00 | NV | 0 | NETA |
| 2 | 1.41 | 0.59 | 1.21 | 0.29 | 0.60 | 0.42 | 100.00 | 0.85 | 100.00 |
| 4 | 2.00 | 0.84 | 2.10 | 0.13 | 0.45 | 0.43 | 3.67 | 1.52 | 43.92 |
| 6 | 2.45 | 1.04 | 2.86 | 0.10 | 0.38 | 0.43 | -0.59 | 1.69 | 10.14 |
| 24 | 4.90 | 2.44 | 7.84 | 0.08 | 0.28 | 0.57 | 25.04 | 2.04 | 16.92 |

□ NETA
■ OESTRADIOL

ACTIVE INGREDIENT PATCH

BACKGROUND OF THE INVENTION

1. Field of the Invention

The transdermal administration, i.e. systemic intake following dermal application, of drugs, such as oestradiol, nitroglycerol, nicotine, selegiline, piroxicam, oestradiol valerate, norethisterone, norethisterone acetate, levonorgestrel etc., to name only a few examples, has the advantage over oral administration of absorption bypassing the gastrointestinal tract and therefore of avoidance of metabolism of the drugs during the first hepatic pass. Hepatic metabolism can result in undesirable concentration ratios between the parent substance and metabolites. Another advantage of transdermal administration lies in the uniformity of the blood levels after absorption of the active ingredients through the skin, since influences such as a varying degree of filling of the gastrointestinal tract, interactions with foods or restricted or accelerated intestinal mobility such as occur with peroral administration do not exist. In the event of any active ingredient-related side effects which occur, a technical system for systemic administration of active ingredient via the skin (transdermal therapeutic system TTS, transdermal (drug) delivery system TD(D)S), called active ingredient patches or patches below, can be removed from the skin and the administration of active ingredient can therefore be interrupted immediately. The systems currently commercially available, for example for oestradiol, the combination of oestradiol and norethisterone acetate, nitroglycerol and scopolamine, or systems undergoing clinical trials, such as systems for testosterone, mainly comprise the active ingredients dissolved in alcoholic solution. Alcohol in direct, prolonged contact with the skin in many cases leads to skin irritation or even to allergies, which force discontinuation of the therapy. This was the reason for the systems described below with alternative absorption promoters or supersaturated systems (in the storage state) without absorption promoters. However, it is precisely the supersaturated systems which are physically unstable. In these patches, the active ingredient or ingredients can recrystallize unpredictably and the permeation of these active ingredients through the skin can thus be reduced in an unpredictable manner. Associated with this is then an inadequate permeation of the active ingredient through the skin, which under certain circumstances can lead to levels falling below the blood level concentration which is therapeutically necessary. Supersaturated patches are metastable and therefore in principle unstable.

As a rule, chemical absorption promoters, azones being the best-known example, modify the structure of the skin such that the skin loses its natural barrier function. The absorption promoters undergo interaction with components of the skin, so that in many cases skin irritation and allergic symptoms result. There is thus an urgent need for skin-compatible, therapeutically reliable and stable active ingredient patches for drugs.

2. Background Art

According to the prior art, the patches for systemic administration of hormones can be divided into three classes:
1. Systems comprising absorption promoters
2. Systems without absorption promoters
3. Systems comprising hydrophilic swellable polymers for stabilizing the supersaturated state 1. Patches with absorption promoters Patches with absorption promoters are by far the largest group, since in the technical literature, for example, oestradiol or gestagenic hormones have been described as substances which permeate with difficulty.

EP-A-0 474 647 describes the use of hydrated aluminium silicate for increasing adhesive strength. A glycol, which also serves as an absorption promoter, is used as the solvent. In addition to their absorption-promoting property, glycols have the side effect of drying out the skin. U.S. Pat. No. 5,023,084 claims progesterones and oestrogens in separate layers, each with the absorption promoter n-decanol. Decanol is a skin-irritating and unpleasantly smelling substance which is not approved for pharmaceuticals. EP-A-0 371 496 (=U.S. Ser. No. 278,625) describes the use of oleic acid, a linear alcohol/lactic acid ester, dipropylene glycol or N-methyl-2-pyrrolidone as absorption promoters. U.S. Pat. No. 5,006,342 claims the use of fentanyl, in addition to oestradiol, with hydrophobic polymers in combination with absorption promoters, such as propylene glycol monolaurate. U.S. Pat. No. 4,906,475 describes the use of a solvent, such as PEG, in combination with an absorption accelerator, such as polysorbate 80. Polysorbate 80 is a surfactant which can destroy the structure of the skin and can thus cause skin damage. EP-A-0 402 407 (=U.S. Ser. No. 160,635) describes the use of a combined absorption promoter of isopropyl myristate and laurin monoglyceride. EP-A-0 430 491 (=AR SN 315 479) claims the use of absorption promoters such as unsaturated fatty acids and esters thereof and glycerol and alkylene-1,2-diols. U.S. Pat. No. 5,053,227 and 5,059,426 claim the use of diethylene glycol monomethyl ether by itself or in combination with an alkyl ester. U.S. Pat. No. 4,956,171 claims the use of a combined enhancer comprising sucrose cocoate and methyl laurate. U.S. Pat. No. 4,996,199 claims the use of tertiary a mines and amides as absorption promoters. U.S. Pat. No. 4,906,169 comprises a multi-layer patch with a layer containing oestradiol and a gestagen-containing layer which additionally contains an absorption promoter.

Absorption promoters of the substance classes described above are potentially harmful to the skin in that, for penetration of drugs into the skin, they must destroy the structure thereof to render it more permeable. In many cases, this results in skin irritation as far as sensitization. Even ethyl alcohol can cause allergies in the event of intensive contact. None of the patches described contains substances to avoid skin irritation.

2. Patches without absorption promoters

Japanese Patent JP-A-02.229 114 describes a patch in which oestradiol is contained in polyvinylpyrrolidone (PVP) in a weight concentration of 3 to 17%. The PVP layer here is in direct contact with the skin over an area of 2 to 40 $cm^2$. PVP is not a pressure-sensitive contact adhesive. This patch additionally requires an edge of adhesive for fixing to the skin. EP-A-0 346 211 (=JP-A-02.196 714, 02.233 617, 03.017 018, 03.044 326 and 03.044.327) claim the use of a copolymer of 2-ethylhexyl acrylate and N-vinyl-2-pyrrolidone without absorption promoters. EP-A-0 272 918 (=U.S. Ser. No. 945,389) describes the use of a macroporous foam in which active ingredient is present in immobilized form. EP-A-0 409 383 (=U.S. Ser. No. 461,676) describes an oestrogen-containing patch in the concentration range from 0.01 to 1% of an oestrogen in combination with a water-insoluble vinylpyrrolidone for retarded release of the active ingredient to the skin. U.S. Pat. No. 4,994,267 describes a mixture of a synthetic or natural rubber in combination with an ethylene/vinyl acetate copolymer and acrylate. AU-A-91.76 582 (=JP SN 90.202 409) describes the use of an acrylate adhesive in combination with a polyester carrier film having a layer thickness of 0.5 to 4.9 μm and an extensibility of a factor of 1 to 5 in one planar direction perpendicular to the other. The inventors claim an adequate absorption of active ingredient merely due to the mechanical effect of the plaster clinging to the skin in an optimum manner because of the extensible film. EP-A-0 416 842 (=U.S. Ser. No. 405,630) expressly describes the use of acrylate copolymers without absorption promoters, which contain active ingredients, preferably oestrogens or norethisterone or norethisterone acetate, by themselves or in combination. These patches described above are merely carriers of drugs, which allow no control over absorption at all. The skin cannot be rendered permeable in a controlled manner to the active ingredient norethisterone acetate and/or oestradiol, which permeates with difficulty, so that the blood levels which are established depend very greatly on the particular type and state of the skin. Such systems generate very widely varying blood levels and cannot guarantee the necessary therapeutic reliability.

Supersaturated plasters, which are described below, also have the fundamental inadequacies just described.

3. Supersaturated systems

EP-A-0 186 019 claims the use of a water-swellable polymer in, for example, a polyisobutylene matrix for retardation of crystallization of the active ingredient present above its saturation concentration. By this means the thermodynamic activity of oestradiol is said to be increased and skin permeation promoted, so that absorption promoters can be dispensed with. However, this measure is also unable to avoid the wide scatter in blood levels. Here also, no measures are taken to reduce skin irritation, which experience shows may always occur with pressure-sensitive contact adhesives.

SUMMARY OF THE INVENTION

The present invention was thus based on the object of developing a reliably acting patch, which at the same time is skin-compatible and can be produced economically, for systemic administration of active ingredients. Examples of active ingredients are summarized in 16 groups below.

The patch should be made of adhesives customary in medicine and other auxiliaries customary from pharmacopoeias (without skin-damaging or potentially skin-damaging properties). It should be possible for the patch to be charged with active ingredients to the highest possible level, without losing any of its adhesive strength, in order to generate uniformly high blood levels over the longest possible time. For this, by way of example, active ingredients such as 17-β-oestradiol, norethisterone acetate and the like were dissolved in the acrylate adhesives or silicone adhesives which can be used medically, and the adhesive strength on human skin, the in vitro release of active ingredient in accordance with the American Pharmacopeia USP XXII, the in vitro skin permeation through the isolated skin of shaved mice or through membranes of adhesive, the recrystallization of the active ingredients incorporated and the water content of patches were investigated, the latter by means of a sensitive electrometric method.

It has now been found that pressure-sensitive acrylate adhesives which are customary in medicine, such as, for example, an acrylate copolymer of Duro-Tak 1753 (National Starch & Chemical, D-Neustadt) indeed have good dissolving properties for oestradiol and norethisterone acetate, but the initial adhesive strength and the long-term adhesive strength leave something to be desired. Pressure-sensitive silicone adhesives are more flexible and have a high initial adhesive strength. However, the dissolving capacity for the abovementioned hormones is very much poorer, thus, for example, the oestradiol of a 2% strength solution in a silicone adhesive (Bio-PSA X7-4602, Dow Corning GmbH, D-Meerbusch) crystallizes out again within about 2 weeks at room temperature. Since only dissolved active ingredient is available for permeation through the skin, the patches must be stable towards recrystallization.

However, in order thus to achieve a high diffusion capacity of the active ingredients incorporated, the patch adhering to the skin should impart to the active ingredients a high thermodynamic activity. As already reported, this is achieved, for example, by a concentration beyond the solubility of the active ingredients in the polymers. These systems are supersaturated and therefore physically unstable. Recrystallization of the active ingredients cannot be controlled, and the thermodynamic activity will therefore decrease uncontrollably during storage of such patches.

The concept that mixtures of pressure-sensitive acrylate and/or silicone adhesives with natural α-tocopherol show an excellent initial and long-term adhesion to skin and at the same time impart to the active ingredients incorporated a high thermodynamic activity after application to the skin is, then, completely surprising. α-Tocopherol is known as vitamin E with its pharmacological actions, but not as a resin for increasing the adhesive capacity of polymers. This is all the more astonishing since admixing of oils, such as silicone oil, in the same amounts leads to a virtually complete loss in adhesive strength. Accordingly, the patch of the present invention contains Vitamin E or a vitamin E derivative selected from the groups of alpha-tocopherol, alpha-tocopherol acetate, alpha-tocopherol succinate and/or alpha-tocopherol nicotinate which can range content from 0.5 to 100% by weight based on the matrix and preferably from 1 to 20% by weight.

In the case of the mixture of polymers, the two polymers are incompatible with one another here in the dried adhesive matrix, and form an emulsion-like cloudy polymer mixture, while the individual components form clear adhesive matrices. Charging of the matrix with active ingredient(s) depends here on the mixing ratio of the polymers and the mixture thereof with α-tocopherol. As the silicone content increases, the solubility in the dried matrix decreases, but the total amount of active ingredients which dissolve in the adhesive matrix can be increased again by α-tocopherol. A defined maximum solubility can thus be established by changing the composition of the two types of adhesive with respect to one another or of the individual adhesives with α-tocopherol. This in turn means that the duration within which active ingredient can be released to the skin can be controlled by this principle. If the polymer mixture is not used and only the polyacrylate is employed, the adhesive strength of the poorly adhering polymer can be increased by α-tocopherol alone. Depending on the polymer and active ingredient, this may be sufficient to increase the adhesive strength in this way and to dispense with admixing of silicone.

DESCRIPTION OF THE PREFERRED EMBODIMENTS

The patch compositions according to the invention described so far are systems which are saturated with a maximum of active ingredient, are stable to storage and do not lead to crystallizations. Thus the finding that the patches thus described produce supersaturated states on the skin itself and thereby increase the thermodynamic activity of the active ingredients beyond that of the storage form was furthermore surprising. The degree of supersaturation depends on the initial water content of the patches and the α-tocopherol content. Furthermore, the supersaturation, and therefore the thermodynamic activity of the active ingredients, can be influenced by carrier films of different "impermeability".

The fact that the active ingredient content in the polymer matrix depends very greatly on the residual water content of the polymer in the part per thousand range was completely unexpected here. Oestradiol may be used as an example of suitable drugs, for further statements. Thus, for example, a matrix comprising acrylate polymer (Durotak 1753) which contains 7.5% of α-tocopherol can dissolve about 2.5% of oestradiol at a water content of 1.2%, while oestradiol is soluble in the matrix thus hydrated in an amount of only 1.3% at a water content of about 3.9%. The determination of the water in the matrix was carried out here with a modified electrometric Karl-Fischer determination method.

The solubility of the oestradiol in the matrix was determined in two ways:

1. Solubility determination in the "dry" matrix

Since determination of the solubility of active ingredients in highly viscous solvents, like the adhesives used here, cannot be carried out in the same way as in liquid systems by a simple concentration measurement of the solvent phase in equilibrium with the sediment, matrices of adhesive of different active ingredient contents were prepared by coating a siliconized carrier film with the active ingredient/adhesive solution and subsequently evaporating off the solvent. Oestradiol seed crystals of precisely defined length were introduced into the resulting matrices of adhesive and the change in crystal dimensions with respect to time was measured. If no changes at all in the size of the crystals occur during the observation period, the active ingredient concentration in the matrix is close to the saturation concentration. The solubility thus determined for oestradiol is about 2.5% by weight in a "dry" system, that is to say a water content of less than 5%.

2. Determination of the oestradiol concentration in a completely hydrated matrix The flow J of a substance through a membrane of defined layer thickness is given by the simplified equation 1 as $$J = \frac{dM}{dt} = \frac{D \times A \times K \times C_0}{h} \quad (1)$$

This relationship indicates the constant flow in the equilibrium state of a diffusion experiment. The amount (M) diffusing through the membrane per unit time (t) is accordingly directly proportional to the concentration on the donor side of the membrane (Co). The other parameters are D diffusion coefficient, A diffusion area, K partition coefficient between the donor and membrane, h thickness of a membrane. The variable J can be determined from the diffusion diagram of. A—the diffusion area—and h—the membrane thickness—can be measured directly, so that the diffusion coefficient and the partition coefficient must still be determined for determination of the concentration.

The diffusion coefficient D can be determined in accordance with the equation $$t_{lag} = \frac{h^2}{6 \times D} \quad (2)$$

from the lag time and the layer thickness of the membrane, so that in the end the partition coefficient K must still be determined. In the case where the donor compartment and the membrane are made of the same material, the partition coefficient K can be assumed to be 1 by approximation. In practice, a procedure can be followed in which a saturated layer of adhesive which contains an excess of the active ingredient in undissolved form is stuck onto an active ingredient-free membrane of the same material of known layer thickness. The passage of the active ingredient through the active ingredient-free membrane with respect to time is then measured in a diffusion cell. The parameters described above can easily be calculated from the typical diffusion curve thereby formed. Since the membrane has hydrated completely by contact with the acceptor medium, water, the resulting saturation concentration is that of a matrix of adhesive containing the maximum amount of water. In the hydrated membrane which is free from active ingredient at the start of the experiment, not more than about 1.3% of oestradiol can dissolve in contact with the saturated layer of adhesive. This applies to a composition of the matrix of 92.5% Durotak 1753 and 7.5% Copherol. If an active ingredient matrix which absorbs 2.5% of oestradiol in the dry state were now to be brought to the state hydrated to the maximum, a supersaturation of about 95% would result due to the reduction in solubility, since the crystallization is inhibited kinetically by the high viscosity of the adhesive. The high viscosity of the matrix of adhesive can maintain this supersaturated state in a stable condition for several days. If a patch is produced from a matrix described in this way, after being stuck to the skin, the matrix can be hydrated by the perspiratio insensibilis and thus become greatly supersaturated with respect to the active ingredient. Supersaturation of the TTS causes—as mentioned above—an increase in the thermodynamic activity and therefore an increase in the force driving diffusion. The supersaturation of the hydrated system after application is thus desirable and also necessary in order to impart a high thermodynamic activity to drugs which permeate with difficulty. It is thereby possible to allow even substances which permeate with difficulty to diffuse through the skin without using absorption promoters. In the examples section, it is shown, as demonstrated with the aid of in vitro skin permeation studies, that the permeation achieves at least equally high permeation rates in comparison with a system with an absorption promoter. The system produced according to the invention thus has the advantage that, during the storage state, it is saturated or close to the saturation concentration and is therefore stable and acquires the increased thermodynamic activity by absorption of water only after being stuck onto the skin. The absorption of water by the matrix can be influenced here by varying the α-tocopherol content. A matrix comprising 2.5% of oestradiol, 5% of α-tocopherol and 92.5% of acrylate adhesive thus contains about 2.6% of water directly after preparation. A matrix comprising 2.5% of oestradiol, 7.5% of α-tocopherol and 90% of acrylate adhesive, on the other hand, contains only 1.2% of water after preparation and drying under identical conditions. The maximum solubility of oestradiol in a matrix of 92.75% of acrylate adhesive and 5% of α-tocopherol is about 2.25% at a residual moisture content of about 2.6% of water. A matrix of 90% of acrylate adhesive and 7.5% of α-tocopherol dissolves about 2.5% of oestradiol at a water content of about 1.2%. The solubility in hydrated matrices, on the other hand, is about 1.3%. Based on the standard commercial dosage of 4 mg of oestradiol per patch, the result is a supersaturation of 1.69 mg in the first case and of 1.92 mg in the second case. This corresponds to an increase in supersaturation and therefore in thermodynamic activity by about 10%. α-Tocopherol can thus determine the degree of supersaturation of hydrated matrices and therefore the diffusion of active ingredients through the skin.

Another possibility for influencing the absorption of water by the matrix and therefore for controlling the degree of supersaturation is offered by the use of carrier films, which influence the evaporation of water to a varying degree after the patches have been stuck onto the skin. The maximum hydration, which has been described in the above case, is obtained by using occlusive films. These include, for example, polyester or polypropylene/polyethylene films. If the release of water from the systems to the environment after the systems have been bonded to the skin is measured, after application to the lower arm at a transepidermal water loss (TEWL) of 7.1 g/m$^2$/hour using polyterephthalic acid ester film (PE, 19 μm), for example, a TEWL of 3.1 g/m$^2$/hour is established. After application of such a plaster for five hours, the TEWL rises to about 40 to 50 g/m$^2$/hour immediately after the patch has been peeled off the skin. The skin is therefore highly hydrated. A patch which contains polyurethane (PU, 40 μm) as the covering film, in contrast, reduces the TEWL to about 5.9 g/m$^2$/hour. After the patch has been peeled off, the value rises to only about 11 g/m$^2$/hour. The skin under such a patch accordingly has a lower degree of hydration compared with the normal state. A matrix covered by film which is permeable to water vapour accordingly will not absorb as much water as a completely covered matrix. The degree of supersaturation therefore becomes removed from the maximum value and permeation falls.

In practice, in the preferred embodiment of the invention, the acrylate polymer can be any desired homopolymer, copolymer or terpolymer comprising various acrylic acid derivatives. In such a preferred embodiment, the acrylic acid polymer makes up from about 2 to about 95% of the total weight in the total dermal composition, and preferably about 2 to about 90%. The amount of acrylate polymer depends on the amount and type of drug used which is incorporated in the medicament used.

The acrylate polymers of this invention are polymers of one or more monomers of acrylic acids and other copolymerizable monomers. The acrylate polymers moreover comprise copolymers of alkyl acrylates and/or methacrylates and/or copolymerizable secondary monomers or monomers having functional groups. If the amount of each type added as a monomer is changed, the cohesive properties and solution properties of the resulting acrylate polymers can be changed. In general, the acrylate polymer comprises at least 50% by weight of an acrylate or alkyl acrylate monomer, 0 to 20% of a functional monomer which can be copolymerized with acrylate, and 0 to 40% of another monomer.

Acrylate monomers which can be used with acrylic acid and methacrylic acid are listed below: butyl methacrylate, hexyl acrylate, hexyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate and tridecyl methacrylate.

The following functional monomers which can be copolymerized with the abovementioned alkyl acrylates or methacrylates can be employed together with acrylic acid and methacrylic acid: maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate and methoxyethyl methacrylate.

Further details and examples of adhesive acrylates which are suitable for the invention are described in Satas' Handbook of Pressure Sensitive Adhesive Technology "Acrylic Adhesives", 2nd edition, pp. 396–456 (D. Satas, Editor), Van Mostrand Reinhold, New York (1989).

Appropriate adhesive acrylates are commercially obtainable under the trade name Duro-Tak and include the polyacrylate adhesive.

Appropriate polysiloxanes include pressure-sensitive silicone adhesives which are based on two main constituents: a polymer or adhesive and a tack-increasing resin. The polysiloxane adhesive is usually formulated with a crosslinking agent for the adhesive, typically a high molecular weight polydiorganosiloxane, and with the resin to provide a three-dimensional silicate structure via an appropriate organic solvent. Admixing of the resin to the polymer is the most important factor for modifying the physical properties of the polysiloxane adhesive. Sobieski et al., "Silicone Pressure Sensitive Adhesives", Handbook of Pressure Sensitive Adhesive Technology, 2nd edition, pp. 508–517 (D. Satas, Editor), Van Nostrand Reinhold, New York (1989).

Appropriate pressure-sensitive silicone adhesives are commercially obtainable under the trade name BIO-PSA X7.

Examples of active medicaments which the patch of this invention can contain are:

1. Circulatory drugs, such as, for example, organic nitrates, such as nitroglycerol isosorbide dinitrate; procainamide; thiazides; dihydropyridines, such as nifedipine or nicardipine; beta blockers, such as timolol or propranolol; ACE inhibitors, such as enalapril, captopril or lisinopril; or alpha-2 blockers, such as clonidine or prazosine.

2. Androgenic steroids, such as testosterone, methyl testosterone or fluoximesterone.

3. Oestrogens, such as oestradiol esters, oestradiol propionate, 17-β-oestradiol, 17-β-oestradiol valerate, oestrone, mestranol, oestriol, 17-β-ethynyloestradiol or diethylstilboestrol.

4. Progestagenic hormones, such as progesterone, 19-Norprogesterone, norethisterone, norethisterone acetate, melengoestrol, chlormadinone, ethisterone, medroxyprogesterone acetate, hydroxyprogesterone caproate, ethynodiol diacetate, 17-α-hydroxyprogesterone, norgestrel and others.

5. Active ingredients having an action on the central nervous system, such as, for example, sedatives, hypnotics, anxiolytics, antidepressants, analgesics and anaesthetics, such as buprenorphine, naloxone, haloperidol, flufenacin, barbitals, lidocaine, mepivacaine, fentanyl, suventanil or nicotine.

6. Agents for treatment of Parkinson's disease, such as selegiline salts or seligiline base, bromocriptine, lisuride and others.

7. Anti-inflammatory active ingredients, such as hydrocortisone, cortisone, dexamethasone, triamcinolone, prednisolone, ibuprofen, naproxen, fenoprofen, flurbiprofen, indoprofen, ketoprofen, piroxicam, diflunisal and others.

8. Antihistamines, such as dimenhydrinate, perfenacin, prometacin, terfenadin and others.

9. Active ingredients having an action on the respiratory tract, such as theophylline or β$_2$-adrenergic agonists, such as albuterol, terbutalin, fenoterol, salbutamol and others.

10. Sympathicomimetics, such as dopamine, phenylpropanolamine, phenylephrine and others.
11. Antimuscarines, such as atropine, scopolamine, homatropine, benzatropine and others.
12. Dermatological active ingredients, such as vitamin A, cyclosporin, dexpanthenol and others.
13. Prostaglandins, such as prostaglandin E1, prostaglandin E2, prostaglandin F2 and analogs.
14. Antioestrogens, such as tamoxifen and 3-hydroxy- and 4-hydroxytamoxifen.
15. Antimigraine agents, such as dihydroergotamine and pizotyline.
16. Antiulcer agents, such as misoprostol, omeprazole, enprostil or ranitidine.

The absolute amount of active ingredient contained in the patch determines the period of time within which continuous administration into the organism is maintained. The highest possible charging of the polymer system with active ingredients is therefore desirable if the application period of a patch is long, i.e. several days to one week.

To increase the solubility of active ingredients further, various additives, such as surfactants, oils or low-volatility solvents, have been tested using the example of a patch comprising two active ingredients, oestradiol and norethisterone acetate, in comparison with α-tocopherol. The surfactants were, for example, sodium laurylsulphate, polyethylene(20)-sorbitan monooleate, sucrose monomyristate (sucrose ester) or other toxicologically acceptable substances. All the additives led to an accelerated recrystallization of the active ingredients incorporated. Pharmaceutically customary oils, such as oleyl oleate, olive oil, soya oil and the like, and solvents, such as propylene glycol, glycerol, polyethylene glycol or diethylene glycol, could indeed delay recrystallization of the active ingredients, but could not suppress crystallization (Table 1). For comparison, Table 2 shows the action of α-tocopherol on the solubility. Thus, 10% of α-tocopherol can stabilize up to 2.5% of oestradiol and 10% of norethisterone acetate in the matrix. This fact is exceptionally unusual, since even good, known solvents, such as oleyl oleate or diethylene glycol, had a poorer action by far. The matrix of adhesive in all cases comprised 80% of the acrylate adhesive and 20% of the silicone adhesive. The content of active ingredients was 2.25% of oestradiol and 8.45% of norethisterone acetate. The auxiliaries were added in amounts of 1 and 5%. The compositions were stored at room temperature in closed polyethylene bags.

TABLE 1

Influence of various auxiliaries on the recrystallization time of oestradiol and norethisterone acetate at room temperature.

| Auxiliary | Concentration | Duration of crystallization |
|---|---|---|
| — | — | <3 weeks |
| Polyethylene(20)-sorbitan monooleate | 1% | <3 weeks |
|  | 5% | <1 week |
| Na lauryl sulphate | 1% | <3 weeks |
|  | 5% | <1 week |
| Sucrose monomyristate | 1% | <3 weeks |
|  | 5% | <2 weeks |
| Oleyl oleate | 1% | <4 weeks |
|  | 5% | <8 weeks |
| Olive oil | 1% | <3 weeks |
|  | 5% | <5 weeks |
| Soya oil | 1% | <3 weeks |
|  | 5% | <5 weeks |

TABLE 1-continued

Influence of various auxiliaries on the recrystallization time of oestradiol and norethisterone acetate at room temperature.

| Auxiliary | Concentration | Duration of crystallization |
|---|---|---|
| Propylene glycol | 1% | <3 weeks |
|  | 5% | <2 weeks |
| Glycerol | 1% | <3 weeks |
|  | 5% | <1 week |
| PEG 400 | 1% | <3 weeks |
|  | 5% | <1 week |
| Diethylene glycol (Transcutol) | 1% | <12 weeks |
|  | 5% | <4 weeks |

COMPARATIVE EXAMPLE 1

In the case of the most stable system, containing 1% Transcutol which is described as an absorption promoter, the invitro skin permeation over 72 h, measured on the isolated skin of hairless female mice, is markedly greater than that of a commercial system including the absorption promoter ethanol (Tab. 2). The crystallization behaviour, however, is unsatisfactory, making it impossible to obtain a storage-stable patch. The adhesion properties of this patch are good, although in specific cases there is mild skin reddening following removal of the patches.

EXAMPLE 1

In the search for additives to avoid reddening of the skin, natural α-tocopherol (for example Copherol, Henkel), which is known from cosmetics for its skin protection function, was first incorporated into the matrix of adhesive. It was found here completely unexpectedly that by addition of varying amounts of α-tocopherol, the concentrations of active ingredient in the matrix of adhesive could be increased considerably without recrystallizations occurring in the observation period (Table 3).

TABLE 3

Influence of α-tocopherol on the recrystallization time of oestradiol and norethisterone acetate. Matrix adhesive as in Table 1.

| Concentrations of active ingredients | Concentration of α-tocopherol | Duration of crystallization |
|---|---|---|
| 2.25%/8.45% Oestradiol/NETA | 1% | <4 weeks |
| 2.25%/8.45% Oestradiol/NETA | 5% | >20 weeks |
| 2.5%/10% Oestradiol/NETA | 10% | >20 weeks |

NETA: = norethisterone acetate

Figure 4:
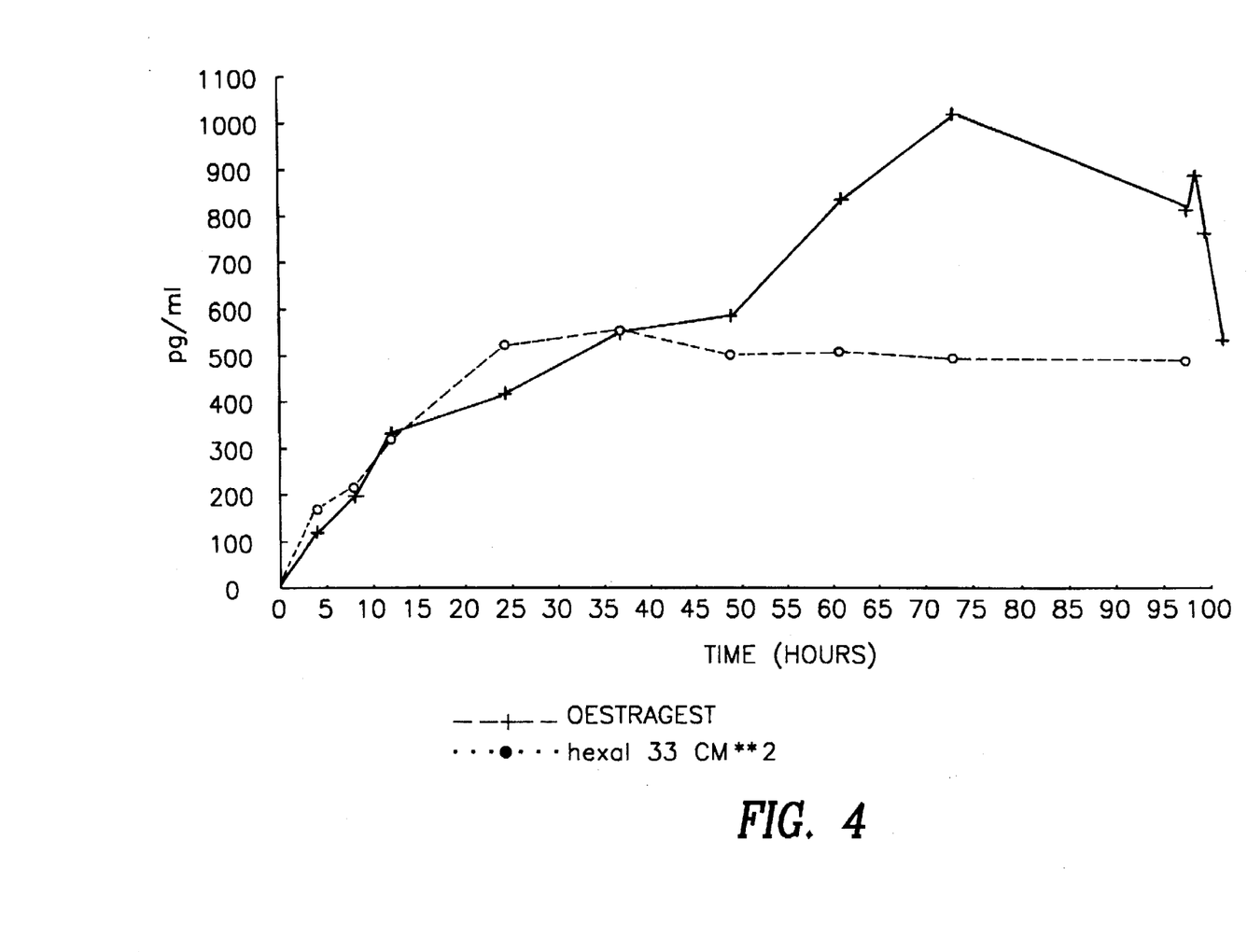
Figure 5A:
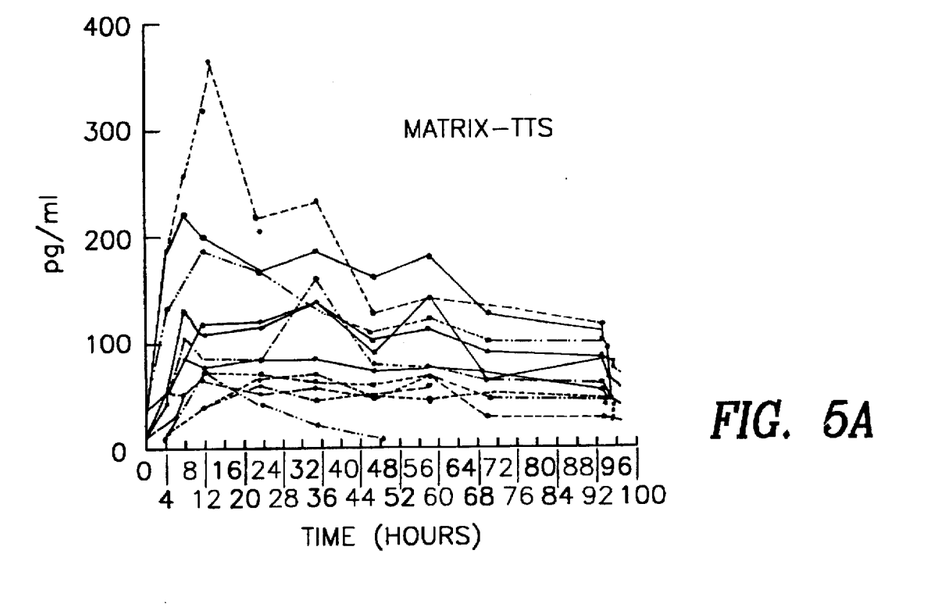
FIGS. 5a–5d and 6a–6d depict, in graph form, oestradiol and NETA plasma levels respectively of matrix patches in comparison with a commercial reservoir system containing ethanol.
Figure 5B:
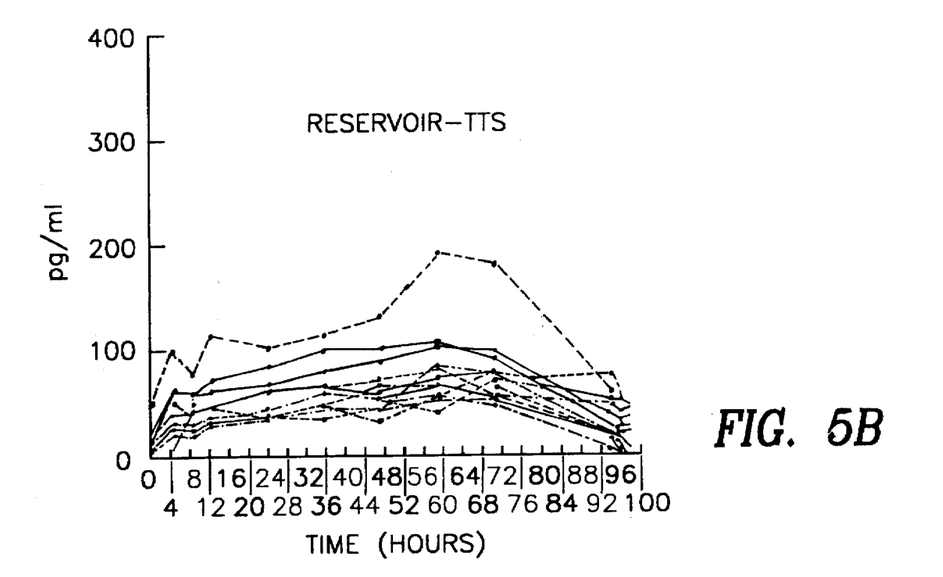
Figure 5C:
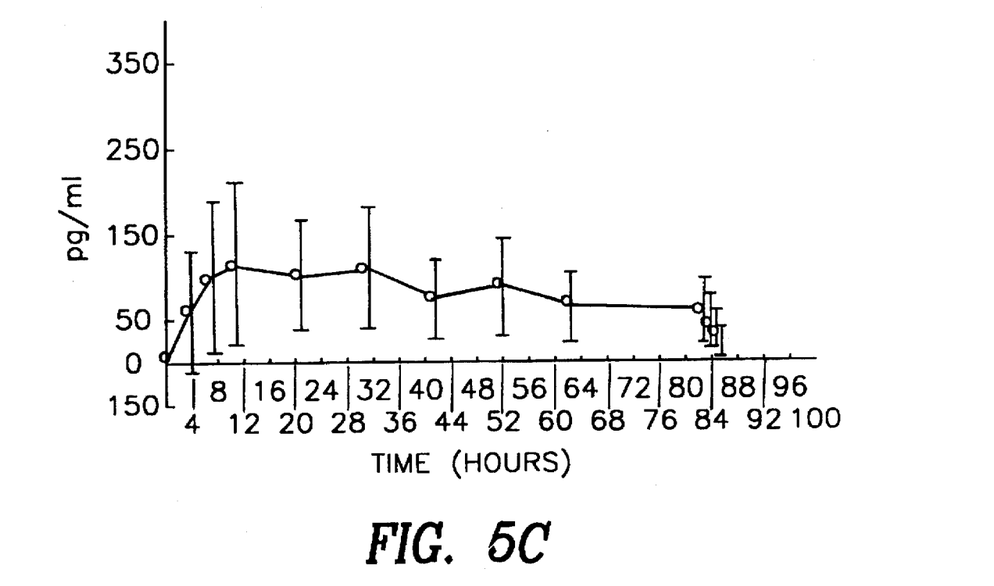
Figure 5D:
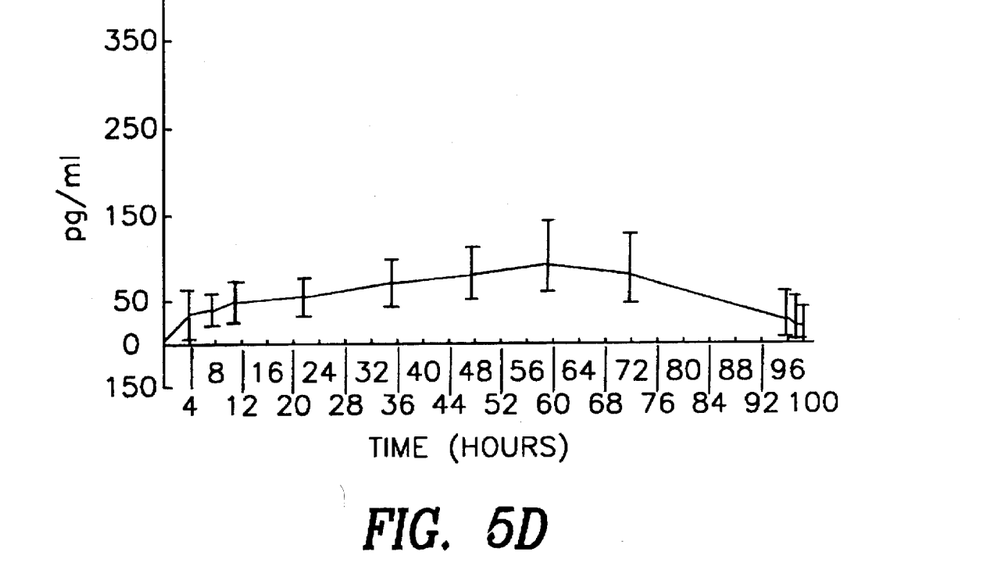
Figure 6A:
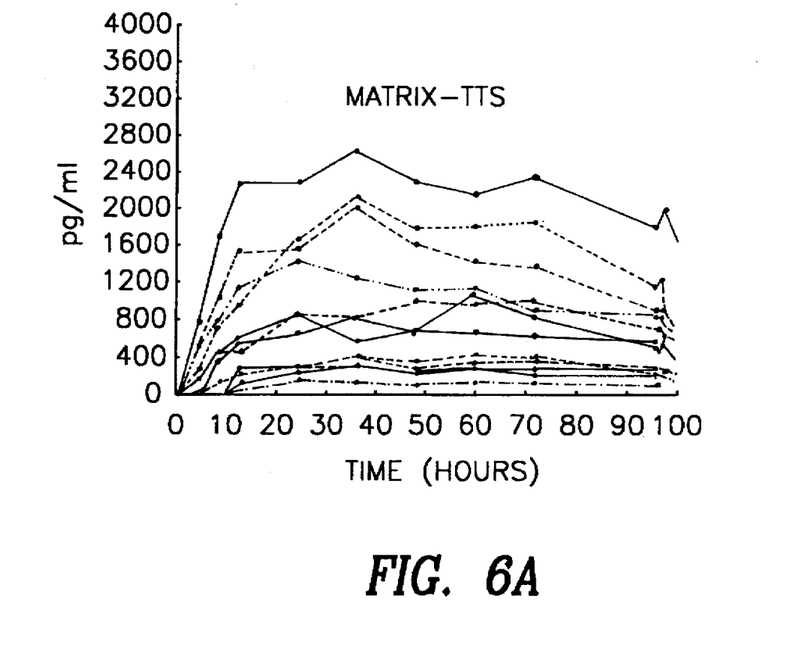
Figure 6B:
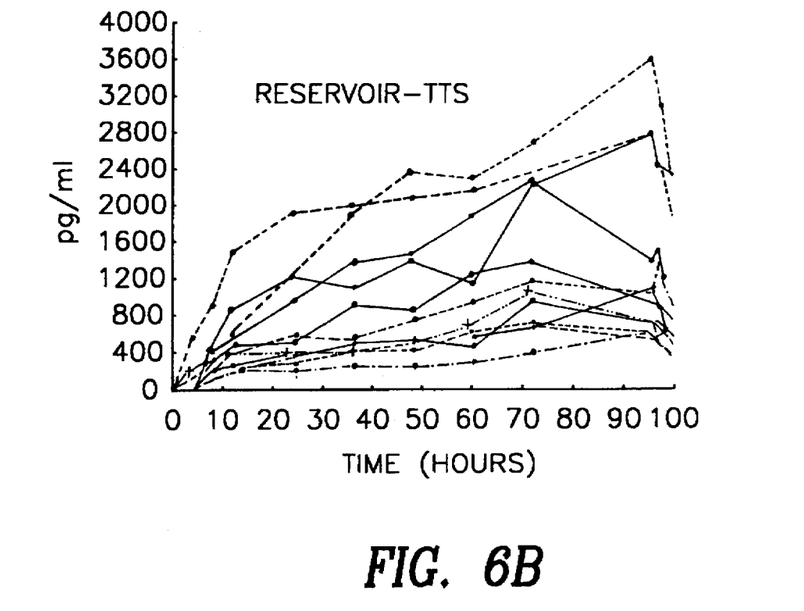
Figure 6C:
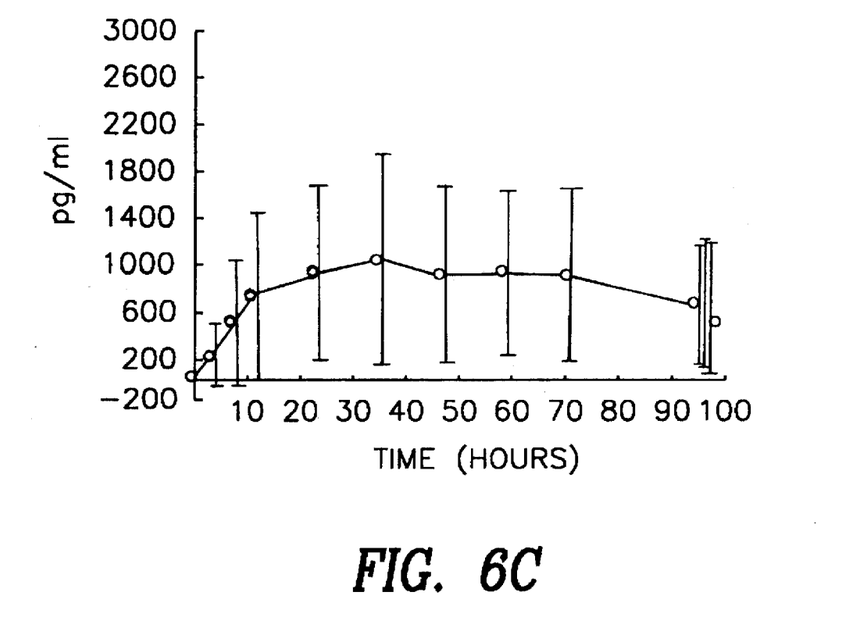
Figure 6D:
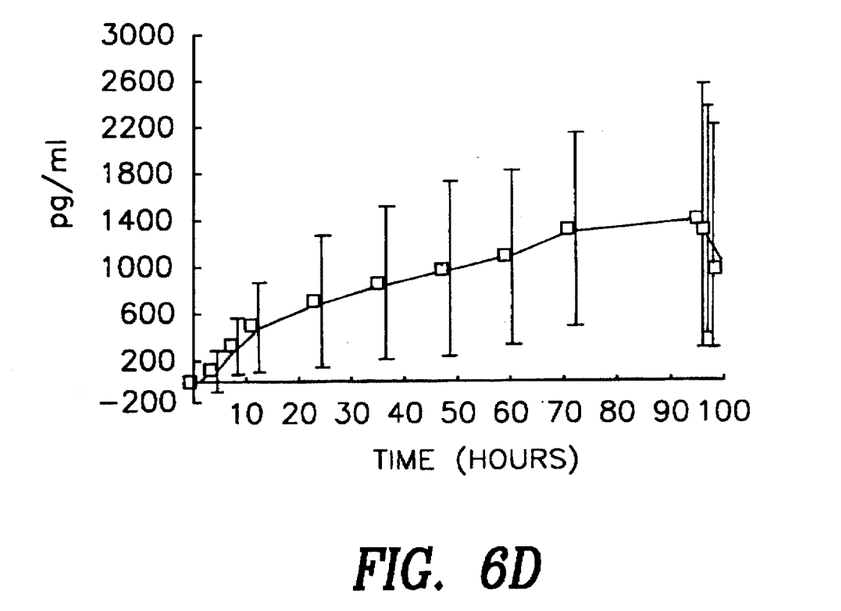

The in vitro skin permeation data of the 2.25/8.45% and 2.5/10% formulations in each case with 5 and 10% of α-tocopherol are summarized in Table 4. FIG. 4 shows the oestradiol plasma level and FIG. 5 shows the NETA plasma level of matrix patches according to the invention, in each case in comparison with a commercial reservoir system containing ethanol.

TABLE 4

In vitro skin permeation of a matrix patch with 5% and 10% of α-tocopherol in comparison with a commercially available ethanol-containing patch of the reservoir type, matrix adhesive as in Table 1.

| Patch | Amount of active compound/48 hours/cm² | |
|---|---|---|
| | Oestradiol | Norethisterone acetate |
| Matrix 5% | 9.3 μg | 15.8 μg |
| Matrix 10% | 10.3 μg | 21.4 μg |
| Reservoir | 2.7 μg | 10.9 μg |

The amounts of active ingredients which have permeated through 1 cm² of skin in 48 hours from the patch containing 5% of α-tocopherol are therefore of the same order of magnitude as in the case of the patch containing transcutol. The concentration of active ingredients in the patch can be increased by increasing the amount of α-tocopherol, and the in vitro skin permeation thus increases significantly. This comparison shows that patches which contain α-tocopherol also have high permeation properties. The permeations are higher for both active ingredients than for a commercially available reservoir system containing ethanol. Furthermore, D-α-tocopherol is a very efficient substance which suppresses recrystallization and allows the concentration of active ingredients in the matrix of adhesive to be almost doubled.

EXAMPLE 2

| Composition | |
|---|---|
| Clonidine | 7.4 g |
| α-Tocopherol (Copherol F 1300) | 10.0 g |
| Durotak 1753 (126–1753) | 41.3 g |
| Durotak 2287 | 41.3 g |

The raw materials were dissolved and the solution was applied to a siliconized film to give a matrix weight per unit area of 96 g/m², a laminate corresponding to Example 1 being produced and stamped out into patches 7(TTS) 10 cm² in size.

The in vitro dissolution was then determined. Test conditions: paddle over disc, demineralized water, 32° C., 900 ml, 50 revolutions/minute, mean value of four releases.

| Time [h] | 0 | 1 | 2 | 4 | 8 | 24 | 32 | 48 |
|---|---|---|---|---|---|---|---|---|
| Release [mg/ 10 cm² TTS] | 0 | 0.43 | 0.62 | 0.91 | 1.35 | 2.48 | 2.85 | 3.67 |

EXAMPLE 3

| Composition | |
|---|---|
| Selegiline | 20 g |
| α-Tocopherol (Copherol F 1300) | 20 g |
| Durotak 1753 (126–1753) | 60 g |

Example 1 was followed for production of patches having a matrix weight per unit area of 90 g/m².

The in vitro dissolution was then determined. Test conditions: paddle over disc, demineralized water, 32° C., 900 ml, 50 revolutions/minute, mean value of four releases.

| Time [h] | 0 | 2 | 4 | 6 |
|---|---|---|---|---|
| Release [mg/20 cm² TTS] | 0 | 14.3 | 18.8 | 20.5 |

The in vitro skin permeation was also determined. Test conditions: modified Franz cell, mouse skin, acceptor 0.9% of NaCl and 0.5% of NaN₃ in water, mean value of two cells.

| Time [h] | 0 | 4 | 8 | 12 | 16 | 20 | 45 |
|---|---|---|---|---|---|---|---|
| Amount permeated [μg/2.5 cm² TTS] | 7 | 140 | 252 | 649 | 775 | 890 | 1570 |

COMPARATIVE EXAMPLE 1

The in vitro skin permeation over 72 hours, measured on the isolated skin of female shaven mice, in the case of the most stable system with 1% of Transcutol, which is described as an absorption promoter, is significantly above that of a commercially available system with the absorption promoter ethanol (Table 2). However, the crystallization properties are unsatisfactory, so that no storage-stable patch can be obtained. The adhesive properties of this patch are good, but in individual cases there is slight reddening of the skin after removal of the patches.

TABLE 2

In vitro skin permeation of a patch with 1% of transcutol in comparison with a commercially available ethanol-containing patch of the reservoir type. Matrix adhesive as in Table 1.

| Plaster type | Amount of active compound/72 hours/cm² | |
|---|---|---|
| | Oestradiol | Norethisterone acetate |
| Matrix | 13.5 μg | 17.8 μg |
| Reservoir | 3.4 μg | 6.5 μg |

USE EXAMPLE 1

| | |
|---|---|
| Oestradiol | 2.0 g |
| α-Tocopherol | 5.0 g |
| Durotak 1753 | 75.0 g |
| Bio-PSA X7-4602 | 18.0 g |

The raw materials described above are mixed until a clear solution is formed. The solution is spread onto a siliconized film or paper so that a content per unit area of 100 g/m² results. A transparent polypropylene or polyester film is laminated onto the dried matrix. The finished patches with sizes of between 10 cm² (corresponding to 2 mg of active ingredient) or 40 cm² (corresponding to 8 mg of active ingredient) are stamped out of the laminate.

The examples show that several desirable effects are achieved by the favourable actions of α-tocopherol in matrices of adhesive:

α-Tocopherol increases the adhesive strength of poorly adhering matrices

α-Tocopherol acts as a skin protection factor.

α-Tocopherol increases the solubility of active ingredients in matrices beyond the extent of conventional oils α-Tocopherol lowers the water content of the matrices of adhesive α-Tocopherol increases the thermodynamic activity of active ingredients in hydrated matrices α-Tocopherol can increase the skin permeation of active ingredients which permeate poorly and therefore also eliminate potentially skin-damaging absorption promoters.

USE EXAMPLE 2

| Oestradiol | 2.5 g |
| α-Tocopherol | 10.0 g |
| Durotak 1753 | 88.0 g |
| Bio-PSA X7-4602 | 7.5 g |

The raw materials are processed to a laminate as in Use Example 1. The patch sizes are 8 cm² (for 2 mg of oestradiol) and 32 cm² (for 8 mg of oestradiol). The matrix weight per unit area here is 100 g/m².

USE EXAMPLE 3 AND COMPARISON USE EXAMPLE 1

| Oestradiol | 2.5 g |
| α-Tocopherol | 7.5 g |
| Durotak 1753 | 90.0 g |

The raw materials are processed to a laminate as in Example 1. The patch sizes are 10 cm² (for 2 mg of oestradiol), 20 cm² (for 4 mg of oestradiol) and 40 cm² (for 8 mg of oestradiol) at a matrix weight per unit area of 80 g/cm². The in vitro skin permeation is shown in Table 5 in comparison with a commercially available oestradiol reservoir patch. Concentration of the matrix patch: 2.5% of oestradiol.

| Patch | Amount of active ingredient/48 hours/cm² Oestradiol |
|---|---|
| Matrix 2.5% | 9.7 μg |
| Reservoir | 5.2 μg |

The blood level courses furthermore were determined with a matrix patch according to the invention (20 cm²) and a commercially available oestradiol reservoir patch. This study was carried out on six healthy female subjects. In each case one matrix patch or one reservoir patch was applied for four days in the randomized cross-over study, the blood level courses being determined by RIA (radioimmunoassay). The base oestradiol blood levels before application of the patches were subtracted from the actual values.

Figure 1A:
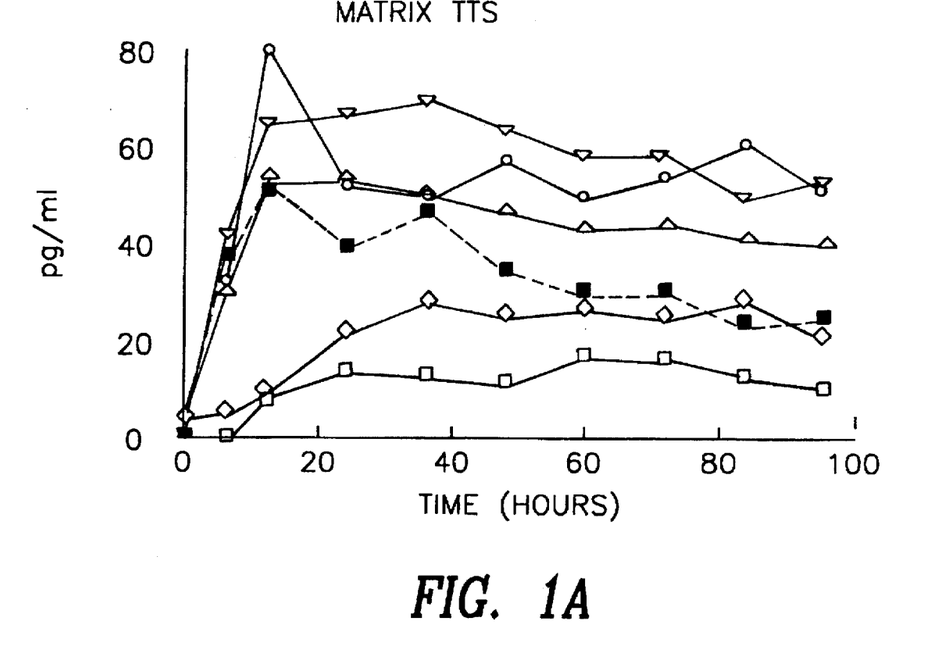
FIGS. 1a–1c shows three graphs depicting Oestradiol plasma levels from matrix patch versus reservoir patch.
Figure 1B:
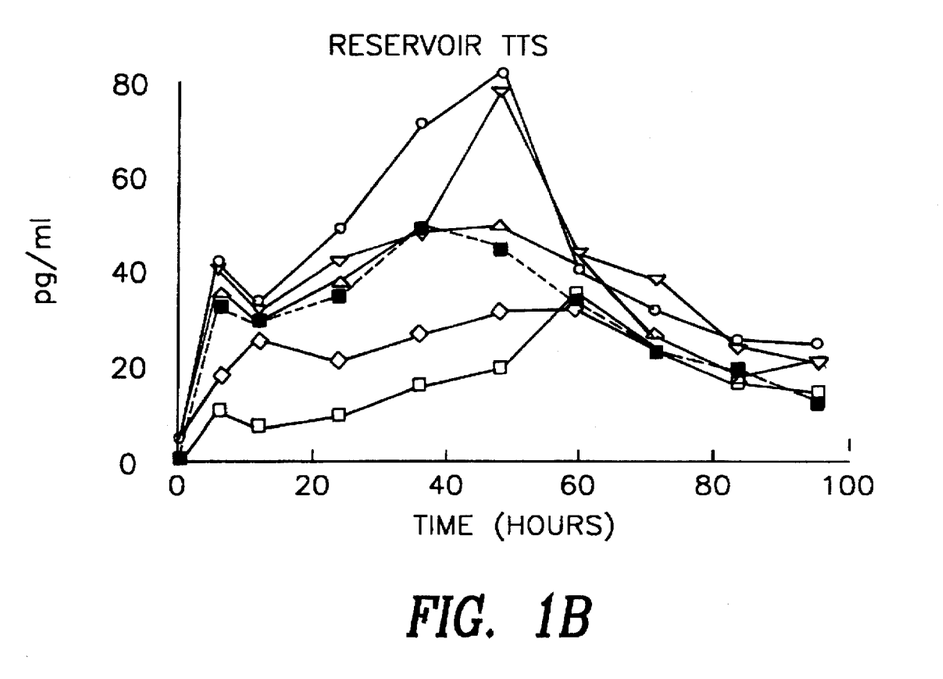
Figure 1C:
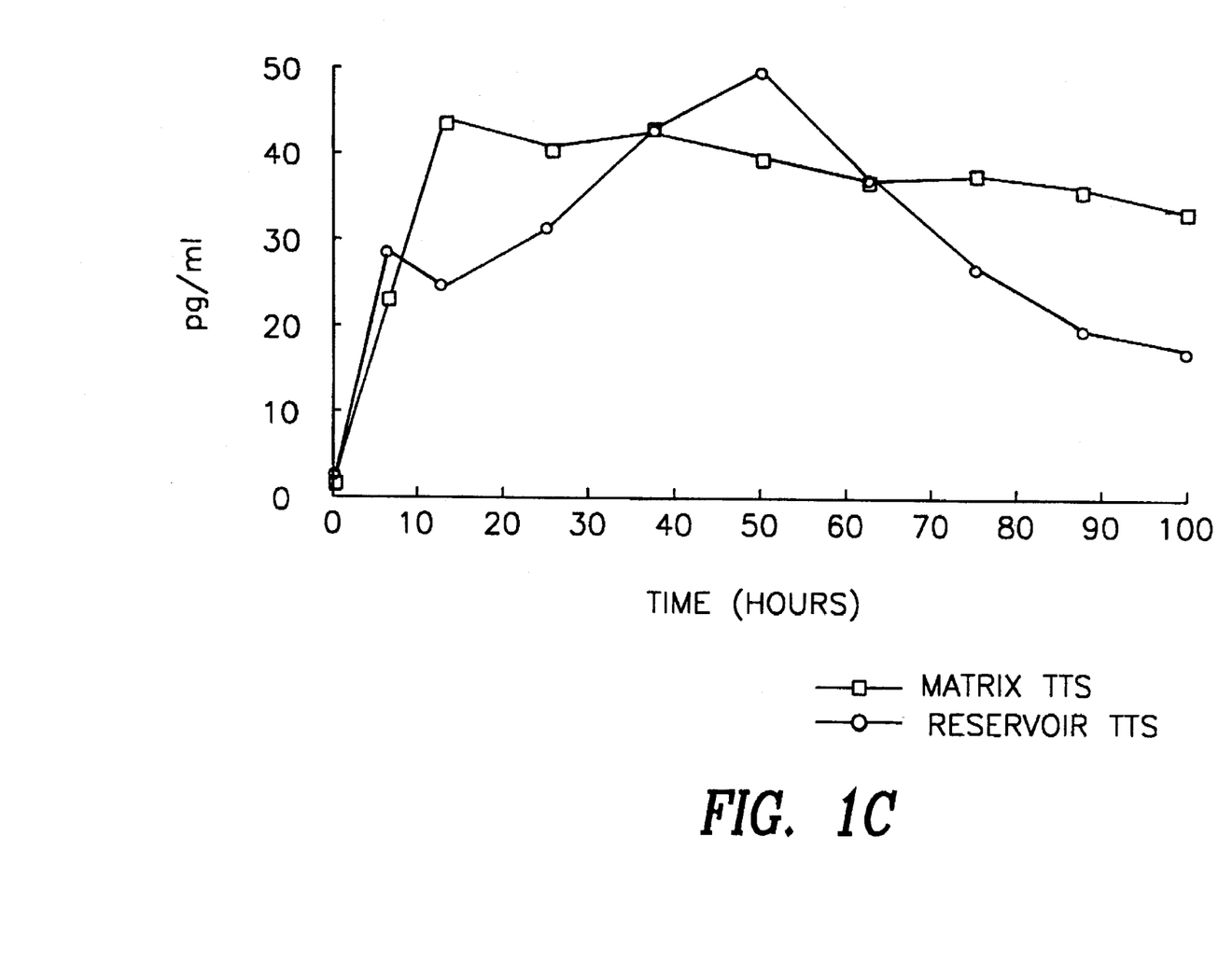
Figure 2A:
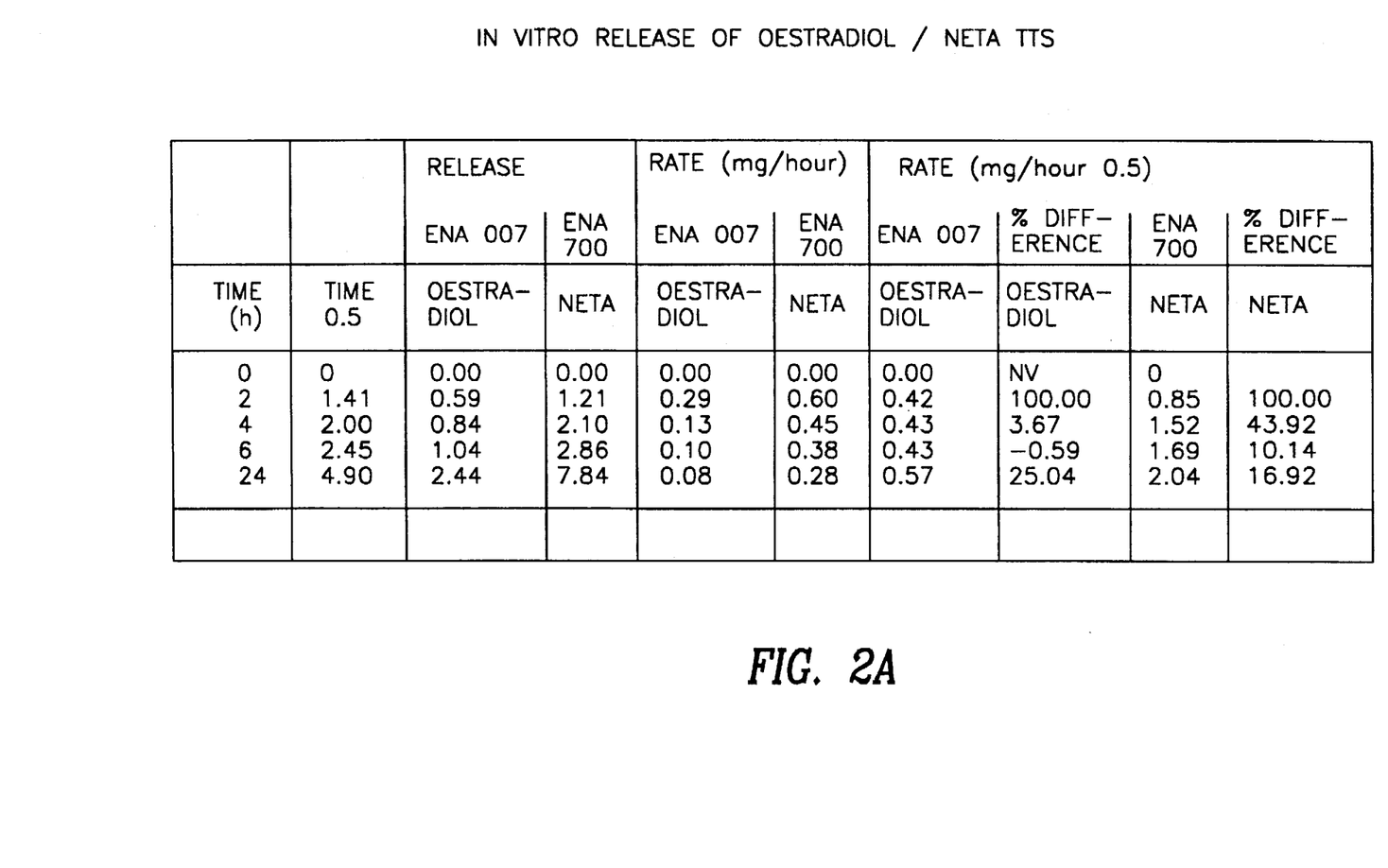
FIGS. 2a–2f shows in table and graph form the in vitro release of oestradiol and norethisterone acetate (NETA).
Figure 2B:
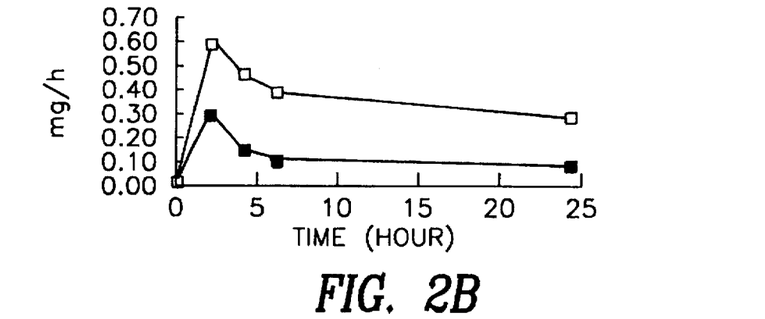
Figure 2C:
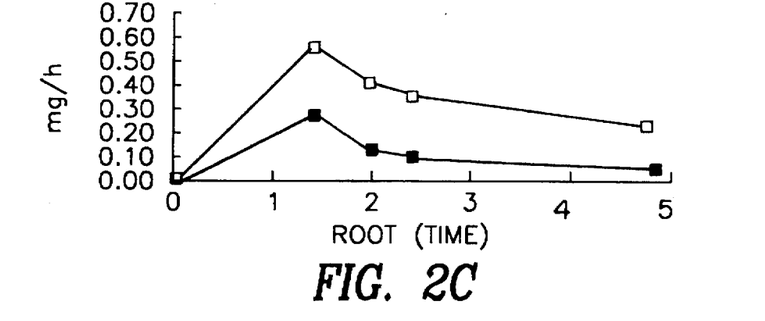
Figure 2D:
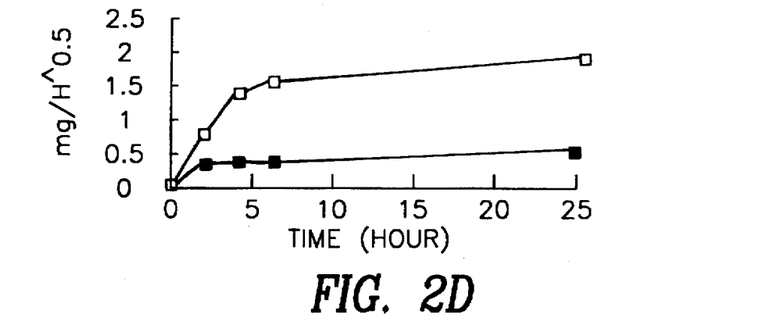
Figure 2E:
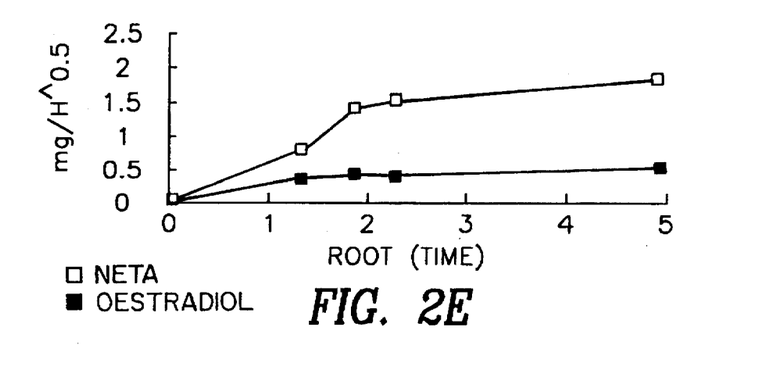
Figure 2F:
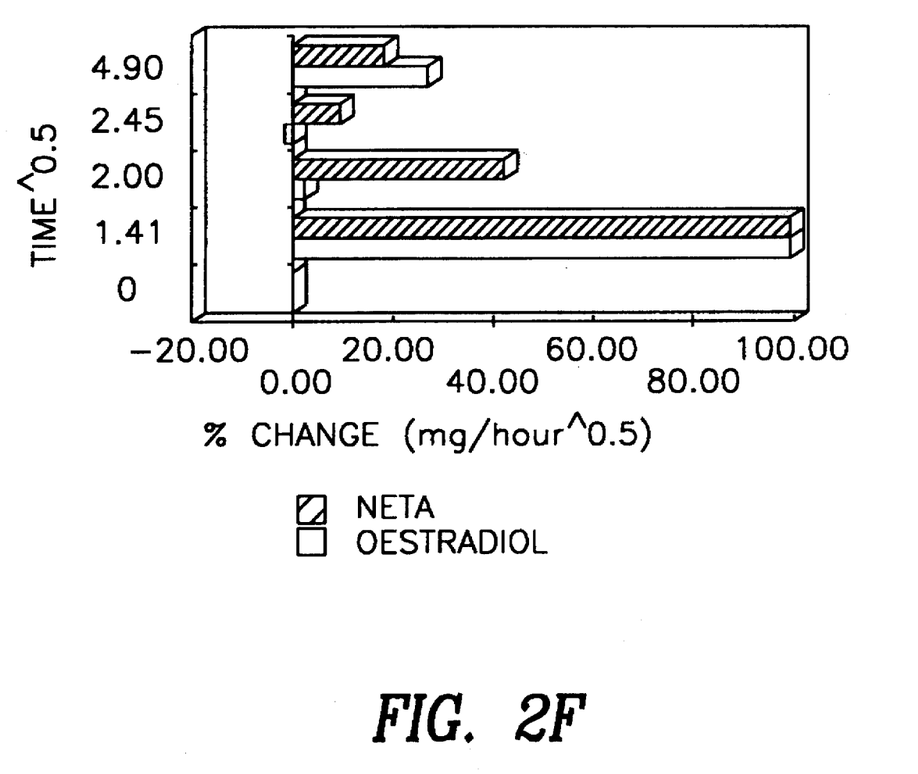

No significant differences were found between the two formulations on statistical analysis of the data (FIG. 1), in particular the areas under the curves which indicate the total amount of oestradiol absorbed. However, the matrix patch according to the invention was distinguished by considerably more uniform and reproducible blood levels, which remained constant over the entire application period, compared with the reservoir patch. A comparison of the symbols in FIG. 1 shows that female subjects with low blood levels exhibited these with both types of application.

USE EXAMPLE 4 AND COMPARISON USE EXAMPLE 2

| Composition | |
|---|---|
| Oestradiol 2.5% | 2.5 g |
| Norethisterone acetate (NETA; 10%) | 10.0 g |
| α-Tocopherol | 10.0 g |
| Durotak 1753 | to 100 g |

Patches according to the invention were produced as in Use Example 3, with the exception that the patch size was 33 cm².

The in vitro release was carried out in accordance with Example 3, the results determined being shown graphically in FIG. 2. In general, the release of active ingredients [mg/hour$^{1/2}$] is constant in the course of time [hours]. In the present case, however, it was found, surprisingly, that the release is not constant in the course of time, but rather a disproportionately high release is to be observed.

Figure 3:
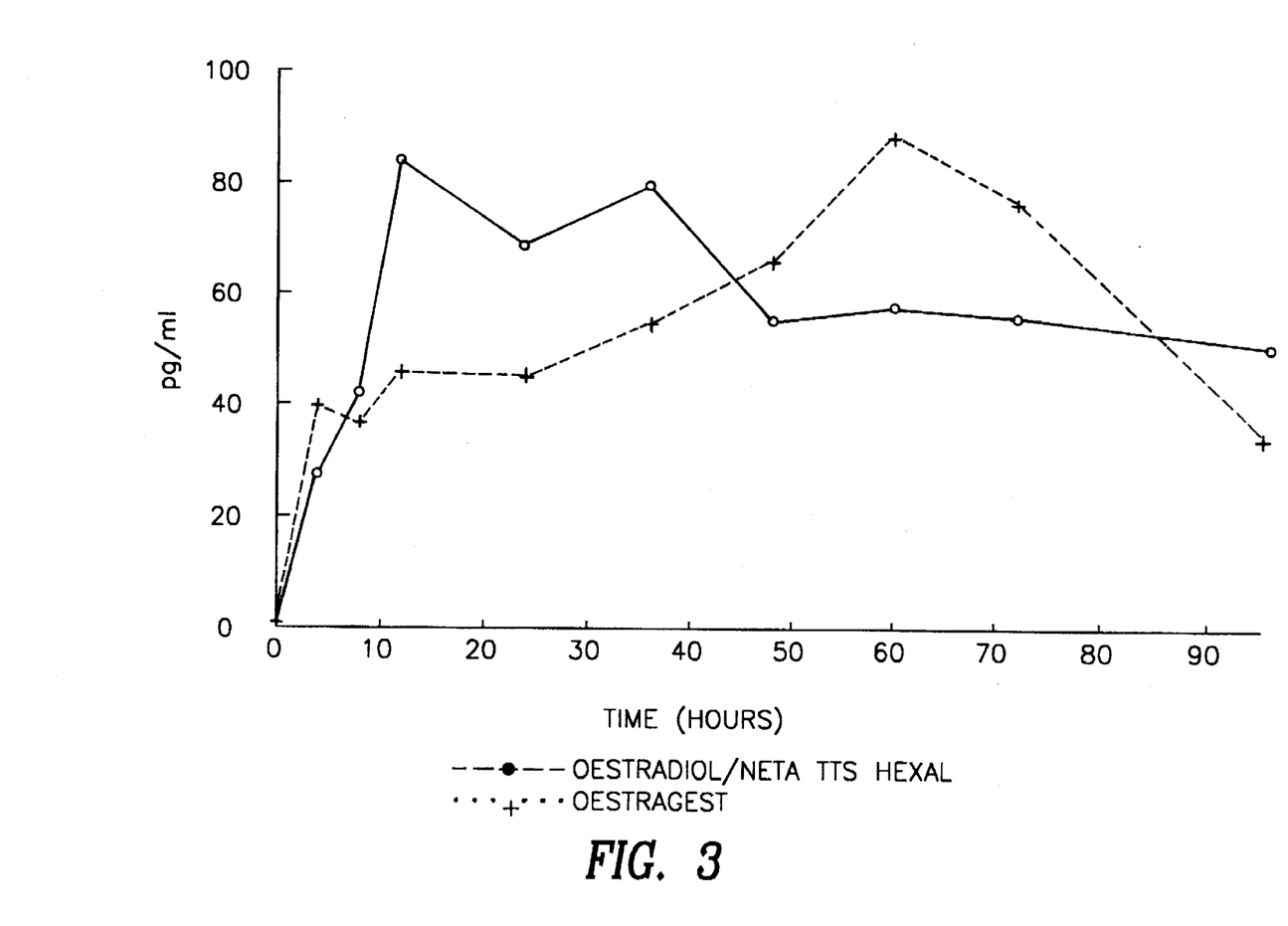
FIGS. 3 and 4 are directed to graphs describing the comparison of plasma levels.

Blood level courses for a combination patch according to the invention and a commercial combination patch were furthermore determined, reference being made to Use Example 3 for this procedure. The plasma oestradiol level can be seen from FIG. 3 (dots for the patch according to the invention and crosses for the comparison patch) and the NETA plasma level can be seen from FIG. 4 (dots for the patch according to the invention and crosses for the comparison patch). FIGS. 3 and 4 show that after about 45 to 50 hours, a constant plasma level is established in the case of the patch according to the invention, which is not achieved with the comparison patch. In addition, destruction of the skin and extensive skin irritation were found with the comparison patch.

COMPARISON USE EXAMPLE 3

| Oestradiol | 2.25 g |
| α-Tocopherol | 5.00 g |
| Norethisterone acetate | 8.45 g |
| Durotak 1753 | 66.97 g |
| Bio-PSA X7-4602 | 22.33 g |

The raw materials are dissolved as in Example 1 and processed on a siliconized film to a weight per unit area of 88.9 g/m² of the dried matrix. Patches of 10 cm² (corresponding to 2 mg of oestradiol/7.5 mg of NETA), 20 cm² (corresponding to 4 mg of oestradiol/15 mg of NETA) or 50 cm² (corresponding to 10 mg of oestradiol/37.5 mg of NETA) are stamped out of the laminate.

COMPARISON USE EXAMPLE 4

| Norethisterone acetate | 10.00 g |
| Durotak 1753 | 87.0 g |
| α-Tocopherol | 10.0 g |

The raw materials are dissolved and applied to a siliconized film to give a matrix weight per unit area of 80 g/m². A laminate is produced therefrom as in Example 1 and stamped to patches 20 cm² (corresponding to 16 mg of NETA) in size.

We claim:

1. An active ingredient patch in the form of a laminate, wherein the concentration of at least one of the active ingredients is such that the saturation concentration of the active ingredient is exceeded on application of the patch to the skin, comprising a carrier and a matrix of a single polymer and having a content of vitamin E or a vitamin E derivative and at least one active ingredient from the group formed by oestrogen hormones and progestagenic hormones, wherein the polymer is a copolymer based on acrylate and comprises at least 50% by weight of alkyl acrylate monomer and optionally, an acrylate monomer copolymerized with acrylic acid.

2. The active ingredient patch of claim 1 wherein the alkyl acrylate monomer is 2-ethylhexyl acrylate.

3. The active ingredient patch according to claim 2 wherein the concentration of at least one of the active ingredients is approximately the saturation concentration in the storage state of the active ingredient patch.

4. The active ingredient patch according to claim 2 wherein the saturation concentration on application of the patch is exceeded in the range from 5 to 100%.

5. The active ingredient patch according to claim 2 wherein the saturation concentration on application of the patch is exceeded in the range from 20 to 80%.

6. The active ingredient patch according to claim 1 contained on a carrier in the form of a film of limited or no permeability to water and water vapour.

7. The active ingredient patch according to claim 1, wherein the vitamin E or vitamin E derivatives is selected from the groups consisting of alpha-tocopherol, alpha-tocopherol acetate, alpha-tocopherol succinate and alpha-tocopherol nicotinate.

8. The active ingredient patch according to claim 7 wherein the content of vitamin E and/or vitamin E derivative is in the range from 1 to 100% by weight, based on the matrix.

9. The active ingredient patch according to claim 7 wherein the content of vitamin E and/or vitamin E derivative is in the range from 0.5 to 20% by weight, based on the matrix.

10. The active ingredient patch according to claim 1 having patch size of up to about 200 cm$^2$ and wherein the active ingredient blood level approaching a therapeutically desirable blood level is achieved by adjustment of the content of vitamin E and/or vitamin E derivative.

* * * * *